US011639529B2

(12) United States Patent
Sanders et al.

(10) Patent No.: US 11,639,529 B2
(45) Date of Patent: *May 2, 2023

(54) EML4-ALK TRANSLOCATIONS IN LUNG CANCER

(71) Applicant: Quest Diagnostics Investments LLC, Secaucus, NJ (US)

(72) Inventors: Heather R. Sanders, Winchester, CA (US); Maher Albitar, Coto De Caza, CA (US); Aurelia Meloni-Ehrig, Gainesville, VA (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/594,718

(22) Filed: Oct. 7, 2019

(65) Prior Publication Data

US 2020/0123617 A1 Apr. 23, 2020

Related U.S. Application Data

(60) Continuation of application No. 15/952,424, filed on Apr. 13, 2018, now Pat. No. 10,435,758, which is a division of application No. 14/928,347, filed on Oct. 30, 2015, now Pat. No. 9,957,573, which is a continuation of application No. 13/518,232, filed as application No. PCT/US2010/060858 on Dec. 16, 2010, now Pat. No. 9,175,350.

(60) Provisional application No. 61/301,551, filed on Feb. 4, 2010, provisional application No. 61/289,234, filed on Dec. 22, 2009.

(51) Int. Cl.
*C12Q 1/6886* (2018.01)
*C07K 16/40* (2006.01)
*C12Q 1/48* (2006.01)

(52) U.S. Cl.
CPC ............ *C12Q 1/6886* (2013.01); *C07K 16/40* (2013.01); *C12Q 1/485* (2013.01); *C12Q 2600/112* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 5,468,613 A | 11/1995 | Erlich et al. | |
| 6,399,364 B1 | 6/2002 | Reeve et al. | |
| 9,175,350 B2 | 11/2015 | Sanders | |
| 9,957,573 B2 | 5/2018 | Sanders | |
| 10,435,758 B2 * | 10/2019 | Sanders | C12Q 1/485 |
| 2002/0182622 A1 | 12/2002 | Nakamura et al. | |
| 2006/0281108 A1 * | 12/2006 | Monforte | C12Q 1/6853 435/6.16 |
| 2008/0090776 A1 | 4/2008 | Mano et al. | |

OTHER PUBLICATIONS

Kleparnik et al. Chem Rev. 2007. 107: 5279-5317 (Year: 2007).*
Takeuchi et al Clinical Cancer Research. 2008. 14(2): 6618-6624 (Year: 2008).*
Sigma Life Science. "qPCR Technical Guide" 2008. p. 1-43, available via URL: <users.stlcc.edu/Departments/fvbio/Thermal_Cycler_sigma%20qpcr_technical_guide.pdf> (Year: 2008).*
Takahashi, T. et al. "Clinicopathologic Features of Non-Small-Cell Lung Cancer with EML4-ALK Fusion Gene". Annals of Surgical Oncology, vol. 17, 2010, pp. 889-897.
Horn, L. et al. "EML4-ALK: Honing In on a New Target in Non-Small-Cell Lung Cancer". Journal of Clinical Oncology, vol. 27 No. 26, Sep. 10, 2009, pp. 4232-4235.
Sanders, H. et al. "Somatic mutations of signaling genes in non-small-cell lung cancer". Cancer Genetics and Cytogenetics, vol. 203, 2010, pp. 7-15.
International Search Report dated Jul. 12, 2011 in Int'l Appl. PCT/US2010/060858 (5 pages.).
Merriam-Webster, "Detect," Free Merriam-Webster Dictionary, http://www.merriam-webster.com/dictionary/detect, accessed May 20, 2014.
The Free Dictionary, "Determining," Free Online Dictionary, http://www.thefreedictionary.com/determining, accessed Mar. 4, 2014.
Fukuyoshi et al., "EML4-ALK fusion transcript is not found in gastrointestinal and breast cancers," British Journal of Cancer, vol. 98, pp. 1536-1539, 2008.
Inamura et al., "EML4-ALK Fusion is Linked to Histological Characteristics in a Subset of Lung Cancers," Journal of Thoracic Oncology, vol. 3, No. 1, pp. 13-17, Jan. 2008.
Choi et al., "Transforming Gene in Non-Small Cell Lung Cancer," Cancer Research, vol. 68, pp. 4971-4976, 2008.
Mitsuhashi et al., "Technical Report: Part 2. Basic Requirements for Designing Optimal PCR Primers," Journal of Clinical Laboratory Analysis, 10:285-293, 1996.
Office Action issued in U.S. Appl. No. 13/518,232 dated Mar. 28, 2014.
Office Action issued in U.S. Appl. No. 13/518,232 dated Sep. 11, 2014.
Office Action issued in U.S. Appl. No. 13/518,232 dated Feb. 6, 2015.
Notice of Allowance issued in U.S. Appl. No. 13/518,232 dated Jun. 22, 2015.
Office Action issued in U.S. Appl. No. 14/928,347 dated Jun. 7, 2017.
Office Action issued in U.S. Appl. No. 14/928,347 dated Oct. 6, 2017.
Notice of Allowance issued in U.S. Appl. No. 14/928,347 dated Dec. 22, 2017.

(Continued)

*Primary Examiner* — Carla J Myers
(74) *Attorney, Agent, or Firm* — Foley & Lardner LLP

(57) ABSTRACT

The present disclosure relates to methods for the diagnosis and evaluation of neoplastic disorders, particularly non-small cell lung cancer. Assays are described in which patient test samples are analyzed for the presence of one or more specific EML4-ALK fusion genes associated with neoplastic disorders.

10 Claims, 2 Drawing Sheets

Specification includes a Sequence Listing.

(56) References Cited

OTHER PUBLICATIONS

Office Action issued in U.S. Appl. No. 15/952,424 dated Aug. 28, 2018.
Office Action issued in U.S. Appl. No. 15/952,424 dated Jan. 28, 2019.
Notice of Allowance issued in U.S. Appl. No. 15/952,424 dated May 24, 2019.

* cited by examiner

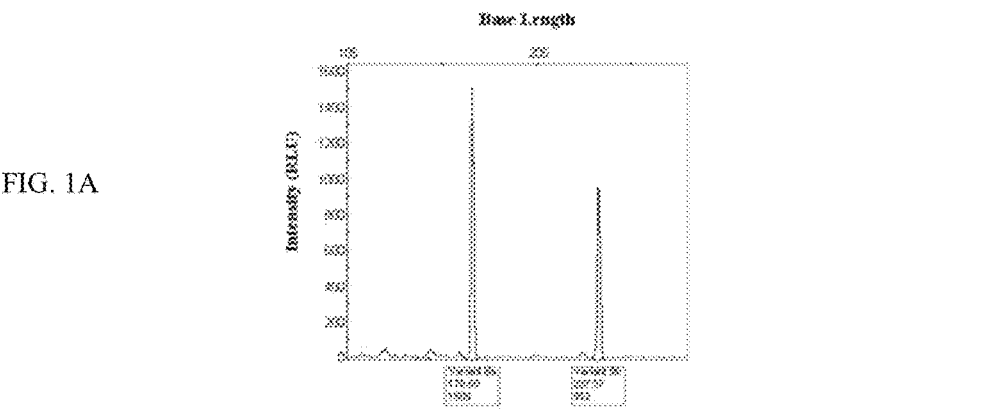
FIG. 1A
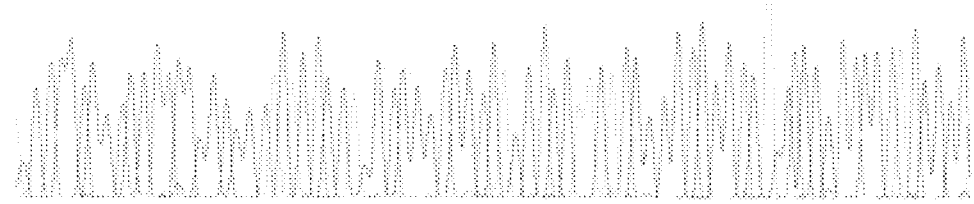
FIG. 1B
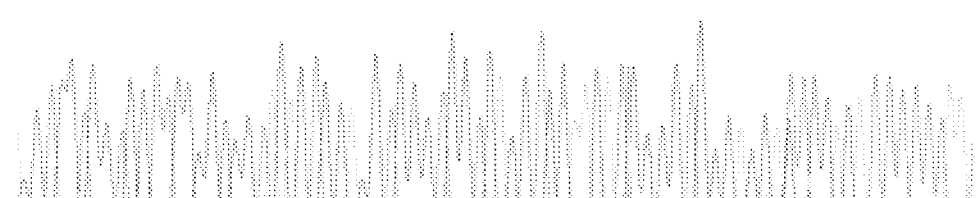
FIG. 1C
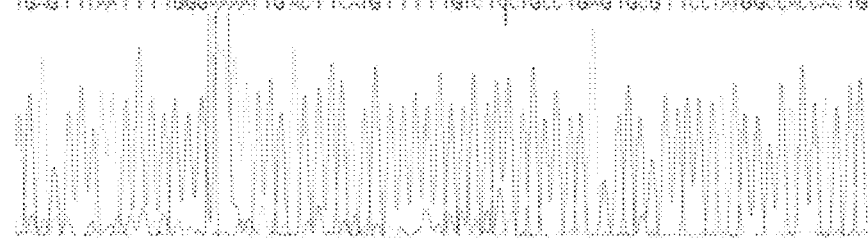

```
                          SEQUENCE LISTING

<160> NUMBER OF SEQ ID NOS: 31

<210> SEQ ID NO 1
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gctcctggtg cttccggcgg tacactgcag gtgggtggtc agctgcaaca tggcctgcct      60
gagtgcgttc ctatggcc                                                   78

<210> SEQ ID NO 2
<211> LENGTH: 143
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gctcctggtg cttccggcgg tacactgcag gtgggtggtc agctgcaaca tggcctggca      60
gcattccaca ttttttaatg agtttaattt tgggaaaatt gacttcatgt ttttgtctcc     120
tgcctgagtg cgttcctatg gcc                                            143

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cggtccgctg aatgaagt                                                   18

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aagatcatgt ggcctcagtg                                                 20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tggtgcaaac agaaaaccaa                                                 20

<210> SEQ ID NO 6
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccctcttcac aacctctcca                                                  20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
acgaccatca ccagctgaaa                                                  20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ctgcagacaa gcataaagat g                                                21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gtcggccaat taccatgttc                                                  20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cttccgaccg ggaaaatagt                                                  20

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
acatcctgac aaaattagga ttgc                                             24

<210> SEQ ID NO 12
<211> LENGTH: 20
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 12
cctctacaac cccacgtcag					20

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
gcatatgctt actgtatggg actg				24

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
tttcacccaa cagatgcaaa					20

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
gactcaggtg gagtcatgc					19

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
aagctcatga tggcagtgtg					20

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
tgtagcagaa ggaaaggcag a					21

<210> SEQ ID NO 18
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 18
gtcttgccac acatcccttc                                                    20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ccaggacact gtgcagattt                                                    20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aggtggtttg ttctggatgc                                                    20

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ccttcctggc tgtaggatct c                                                  21

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cagatatgga aggtgcactg                                                    20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
attccaaatg gctgcaaact                                                    20

<210> SEQ ID NO 24
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 24
agctgttgcc gatgactttt                                                 20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
agcttgctca gcttgtactc                                                 20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cggcggtaca ctgcaggtgg                                                 20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gcaacatggc ctgcctgagt                                                 20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tttttgtctc ctgcctgagt                                                 20

<210> SEQ ID NO 29
<211> LENGTH: 660
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Asp Gly Phe Ala Gly Ser Leu Asp Asp Ser Ile Ser Ala Ala Ser
1               5                   10                  15

Thr Ser Asp Val Gln Asp Arg Leu Ser Ala Leu Glu Ser Arg Val Gln
                20                  25                  30

Gln Gln Glu Asp Glu Ile Thr Val Leu Lys Ala Ala Leu Ala Asp Val
        35                  40                  45
```

-continued

```
Leu Arg Arg Leu Ala Ile Ser Glu Asp His Val Ala Ser Val Lys Lys
    50                  55                  60

Ser Val Ser Ser Lys Gly Gln Pro Ser Pro Arg Ala Val Ile Pro Met
65                  70                  75                  80

Ser Cys Ile Thr Asn Gly Ser Gly Ala Asn Arg Lys Pro Ser His Thr
                85                  90                  95

Ser Ala Val Ser Ile Ala Gly Lys Glu Thr Leu Ser Ser Ala Ala Lys
            100                 105                 110

Ser Gly Thr Glu Lys Lys Lys Glu Lys Pro Gln Gly Gln Arg Glu Lys
            115                 120                 125

Lys Glu Glu Ser His Ser Asn Asp Gln Ser Pro Gln Ile Arg Ala Ser
    130                 135                 140

Pro Ser Pro Gln Pro Ser Ser Gln Pro Leu Gln Ile His Arg Gln Thr
145                 150                 155                 160

Pro Glu Ser Lys Asn Ala Thr Pro Thr Lys Ser Ile Lys Arg Pro Ser
                165                 170                 175

Pro Ala Glu Lys Ser His Asn Ser Trp Glu Asn Ser Asp Asp Ser Arg
            180                 185                 190

Asn Lys Leu Ser Lys Ile Pro Ser Thr Pro Lys Leu Ile Pro Lys Val
    195                 200                 205

Thr Lys Thr Ala Asp Lys His Lys Asp Val Ile Ile Asn Gln Glu Gly
210                 215                 220

Glu Tyr Ile Lys Met Phe Met Arg Gly Arg Pro Ile Thr Met Phe Ile
225                 230                 235                 240

Pro Ser Asp Val Asp Asn Tyr Asp Asp Ile Arg Thr Glu Leu Pro Pro
                245                 250                 255

Glu Lys Leu Lys Leu Glu Trp Ala Tyr Gly Tyr Arg Gly Lys Asp Cys
            260                 265                 270

Arg Ala Asn Val Tyr Leu Leu Pro Thr Gly Glu Ile Val Tyr Phe Ile
    275                 280                 285

Ala Ser Val Val Val Leu Phe Asn Tyr Glu Glu Arg Thr Gln Arg His
    290                 295                 300

Tyr Leu Gly His Thr Asp Cys Val Lys Cys Leu Ala Ile His Pro Asp
305                 310                 315                 320

Lys Ile Arg Ile Ala Thr Gly Gln Ile Ala Gly Val Asp Lys Asp Gly
                325                 330                 335

Arg Pro Leu Gln Pro His Val Arg Val Trp Asp Ser Val Thr Leu Ser
            340                 345                 350

Thr Leu Gln Ile Ile Gly Leu Gly Thr Phe Glu Arg Gly Val Gly Cys
    355                 360                 365

Leu Asp Phe Ser Lys Ala Asp Ser Gly Val His Leu Cys Val Ile Asp
    370                 375                 380

Asp Ser Asn Glu His Met Leu Thr Val Trp Asp Trp Gln Lys Lys Ala
385                 390                 395                 400

Lys Gly Ala Glu Ile Lys Thr Thr Asn Glu Val Val Leu Ala Val Glu
                405                 410                 415

Phe His Pro Thr Asp Ala Asn Thr Ile Ile Thr Cys Gly Lys Ser His
            420                 425                 430

Ile Phe Phe Trp Thr Trp Ser Gly Asn Ser Leu Thr Arg Lys Gln Gly
    435                 440                 445

Ile Phe Gly Lys Tyr Glu Lys Pro Lys Phe Val Gln Cys Leu Ala Phe
    450                 455                 460
```

```
Leu Gly Asn Gly Asp Val Leu Thr Gly Asp Ser Gly Val Met Leu
465                 470                 475                 480

Ile Trp Ser Lys Thr Thr Val Glu Pro Thr Pro Gly Lys Gly Pro Lys
                485                 490                 495

Gly Val Tyr Gln Ile Ser Lys Gln Ile Lys Ala His Asp Gly Ser Val
            500                 505                 510

Phe Thr Leu Cys Gln Met Arg Asn Gly Met Leu Leu Thr Gly Gly
        515                 520                 525

Lys Asp Arg Lys Ile Ile Leu Trp Asp His Asp Leu Asn Pro Glu Arg
530                 535                 540

Glu Ile Glu Val Pro Asp Gln Tyr Gly Thr Ile Arg Ala Val Ala Glu
545                 550                 555                 560

Gly Lys Ala Asp Gln Phe Leu Val Gly Thr Ser Arg Asn Phe Ile Leu
                565                 570                 575

Arg Gly Thr Phe Asn Asp Gly Phe Gln Ile Glu Val Gln Gly His Thr
            580                 585                 590

Asp Glu Leu Trp Gly Leu Ala Thr His Pro Phe Lys Asp Leu Leu Leu
        595                 600                 605

Thr Cys Ala Gln Asp Arg Gln Val Cys Leu Trp Asn Ser Met Glu His
    610                 615                 620

Arg Leu Glu Trp Thr Arg Leu Val Asp Glu Pro Gly His Cys Ala Asp
625                 630                 635                 640

Phe His Pro Ser Gly Thr Val Val Ala Ile Gly Thr His Ser Gly Arg
                645                 650                 655

Pro Cys Cys Ser
            660

<210> SEQ ID NO 30
<211> LENGTH: 1250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Asp Gly Phe Ala Gly Ser Leu Asp Asp Ser Ile Ser Ala Ala Ser
1               5                   10                  15

Thr Ser Asp Val Gln Asp Arg Leu Ser Ala Leu Glu Ser Arg Val Gln
                20                  25                  30

Gln Gln Glu Asp Glu Ile Thr Val Leu Lys Ala Ala Leu Ala Asp Val
            35                  40                  45

Leu Arg Arg Leu Ala Ile Ser Glu Asp His Val Ala Ser Val Lys Lys
        50                  55                  60

Ser Val Ser Ser Lys Gly Gln Pro Ser Pro Arg Ala Val Ile Pro Met
65                  70                  75                  80

Ser Cys Ile Thr Asn Gly Ser Gly Ala Asn Arg Lys Pro Ser His Thr
                85                  90                  95

Ser Ala Val Ser Ile Ala Gly Lys Glu Thr Leu Ser Ser Ala Ala Lys
            100                 105                 110

Ser Gly Thr Glu Lys Lys Lys Glu Lys Pro Gln Gly Gln Arg Glu Lys
        115                 120                 125

Lys Glu Glu Ser His Ser Asn Asp Gln Ser Pro Gln Ile Arg Ala Ser
    130                 135                 140
```

-continued

Pro Ser Pro Gln Pro Ser Ser Gln Pro Leu Gln Ile His Arg Gln Thr
145                 150                 155                 160

Pro Glu Ser Lys Asn Ala Thr Pro Thr Lys Ser Ile Lys Arg Pro Ser
                165                 170                 175

Pro Ala Glu Lys Ser His Asn Ser Trp Glu Asn Ser Asp Asp Ser Arg
            180                 185                 190

Asn Lys Leu Ser Lys Ile Pro Ser Thr Pro Lys Leu Ile Pro Lys Val
        195                 200                 205

Thr Lys Thr Ala Asp Lys His Lys Asp Val Ile Ile Asn Gln Glu Gly
    210                 215                 220

Glu Tyr Ile Lys Met Phe Met Arg Gly Arg Pro Ile Thr Met Phe Ile
225                 230                 235                 240

Pro Ser Asp Val Asp Asn Tyr Asp Asp Ile Arg Thr Glu Leu Pro Pro
                245                 250                 255

Glu Lys Leu Lys Leu Glu Trp Ala Tyr Gly Tyr Arg Gly Lys Asp Cys
            260                 265                 270

Arg Ala Asn Val Tyr Leu Leu Pro Thr Gly Glu Ile Val Tyr Phe Ile
        275                 280                 285

Ala Ser Val Val Val Leu Phe Asn Tyr Glu Glu Arg Thr Gln Arg His
    290                 295                 300

Tyr Leu Gly His Thr Asp Cys Val Lys Cys Leu Ala Ile His Pro Asp
305                 310                 315                 320

Lys Ile Arg Ile Ala Thr Gly Gln Ile Ala Gly Val Asp Lys Asp Gly
                325                 330                 335

Arg Pro Leu Gln Pro His Val Arg Val Trp Asp Ser Val Thr Leu Ser
            340                 345                 350

Thr Leu Gln Ile Ile Gly Leu Gly Thr Phe Glu Arg Gly Val Gly Cys
        355                 360                 365

Leu Asp Phe Ser Lys Ala Asp Ser Gly Val His Leu Cys Val Ile Asp
    370                 375                 380

Asp Ser Asn Glu His Met Leu Thr Val Trp Asp Trp Gln Lys Lys Ala
385                 390                 395                 400

Lys Gly Ala Glu Ile Lys Thr Thr Asn Glu Val Val Leu Ala Val Glu
                405                 410                 415

Phe His Pro Thr Asp Ala Asn Thr Ile Ile Thr Cys Gly Lys Ser His
            420                 425                 430

Ile Phe Phe Trp Thr Trp Ser Gly Asn Ser Leu Thr Arg Lys Gln Gly
        435                 440                 445

Ile Phe Gly Lys Tyr Glu Lys Pro Lys Phe Val Gln Cys Leu Ala Phe
    450                 455                 460

Leu Gly Asn Gly Asp Val Leu Thr Gly Asp Ser Gly Gly Val Met Leu
465                 470                 475                 480

Ile Trp Ser Lys Thr Thr Val Glu Pro Thr Pro Gly Lys Gly Pro Lys
                485                 490                 495

Gly Val Tyr Gln Ile Ser Lys Gln Ile Lys Ala His Asp Gly Ser Val
            500                 505                 510

Phe Thr Leu Cys Gln Met Arg Asn Gly Met Leu Leu Thr Gly Gly Gly
        515                 520                 525

Lys Asp Arg Lys Ile Ile Leu Trp Asp His Asp Leu Asn Pro Glu Arg
    530                 535                 540

Glu Ile Glu Val Pro Asp Gln Tyr Gly Thr Ile Arg Ala Val Ala Glu
545                 550                 555                 560

```
Gly Lys Ala Asp Gln Phe Leu Val Gly Thr Ser Arg Asn Phe Ile Leu
                565                 570                 575
Arg Gly Thr Phe Asn Asp Gly Phe Gln Ile Glu Val Gln Gly His Thr
            580                 585                 590
Asp Glu Leu Trp Gly Leu Ala Thr His Pro Phe Lys Asp Leu Leu Leu
        595                 600                 605
Thr Cys Ala Gln Asp Arg Gln Val Cys Leu Trp Asn Ser Met Glu His
    610                 615                 620
Arg Leu Glu Trp Thr Arg Leu Val Asp Glu Pro Gly His Cys Ala Asp
625                 630                 635                 640
Phe His Pro Ser Gly Thr Val Val Ala Ile Gly Thr Ser Ser Gly Arg
                645                 650                 655
Arg Gln Lys His Glu Val Asn Phe Pro Lys Ile Lys Leu Ile Lys Lys
            660                 665                 670
Cys Gly Met Leu Pro Gly His Val Ala Ala Asp His Pro Pro Ala Val
        675                 680                 685
Tyr Arg Arg Lys His Gln Glu Leu Gln Ala Met Gln Met Glu Leu Gln
    690                 695                 700
Ser Pro Glu Tyr Lys Leu Ser Lys Leu Arg Thr Ser Thr Ile Met Thr
705                 710                 715                 720
Asp Tyr Asn Pro Asn Tyr Cys Phe Ala Gly Lys Thr Ser Ser Ile Ser
                725                 730                 735
Asp Leu Lys Glu Val Pro Arg Lys Asn Ile Thr Leu Ile Arg Gly Leu
            740                 745                 750
Gly His Gly Ala Phe Gly Glu Val Tyr Glu Gly Gln Val Ser Gly Met
        755                 760                 765
Pro Asn Asp Pro Ser Pro Leu Gln Val Ala Val Lys Thr Leu Pro Glu
    770                 775                 780
Val Cys Ser Glu Gln Asp Glu Leu Asp Phe Leu Met Glu Ala Leu Ile
785                 790                 795                 800
Ile Ser Lys Phe Asn His Gln Asn Ile Val Arg Cys Ile Gly Val Ser
                805                 810                 815
Leu Gln Ser Leu Pro Arg Phe Ile Leu Leu Glu Leu Met Ala Gly Gly
            820                 825                 830
Asp Leu Lys Ser Phe Leu Arg Glu Thr Arg Pro Arg Pro Ser Gln Pro
        835                 840                 845
Ser Ser Leu Ala Met Leu Asp Leu Leu His Val Ala Arg Asp Ile Ala
    850                 855                 860
Cys Gly Cys Gln Tyr Leu Glu Glu Asn His Phe Ile His Arg Asp Ile
865                 870                 875                 880
Ala Ala Arg Asn Cys Leu Leu Thr Cys Pro Gly Pro Gly Arg Val Ala
                885                 890                 895
Lys Ile Gly Asp Phe Gly Met Ala Arg Asp Ile Tyr Arg Ala Ser Tyr
            900                 905                 910
Tyr Arg Lys Gly Gly Cys Ala Met Leu Pro Val Lys Trp Met Pro Pro
        915                 920                 925
Glu Ala Phe Met Glu Gly Ile Phe Thr Ser Lys Thr Asp Thr Trp Ser
    930                 935                 940
Phe Gly Val Leu Leu Trp Glu Ile Phe Ser Leu Gly Tyr Met Pro Tyr
945                 950                 955                 960
Pro Ser Lys Ser Asn Gln Glu Val Leu Glu Phe Val Thr Ser Gly Gly
                965                 970                 975
```

Arg Met Asp Pro Pro Lys Asn Cys Pro Gly Pro Val Tyr Arg Ile Met
            980                 985                 990

Thr Gln Cys Trp Gln His Gln Pro  Glu Asp Arg Pro Asn  Phe Ala Ile
            995                 1000                1005

Ile Leu Glu Arg Ile Glu Tyr  Cys Thr Gln Asp Pro  Asp Val Ile
        1010                1015                1020

Asn Thr  Ala Leu Pro Ile Glu  Tyr Gly Pro Leu Val  Glu Glu Glu
        1025                1030                1035

Glu Lys  Val Pro Val Arg Pro  Lys Asp Pro Glu Gly  Val Pro Pro
        1040                1045                1050

Leu Leu  Val Ser Gln Gln Ala  Lys Arg Glu Glu Glu  Arg Ser Pro
        1055                1060                1065

Ala Ala  Pro Pro Pro Leu Pro  Thr Thr Ser Ser Gly  Lys Ala Ala
        1070                1075                1080

Lys Lys  Pro Thr Ala Ala Glu  Ile Ser Val Arg Val  Pro Arg Gly
        1085                1090                1095

Pro Ala  Val Glu Gly Gly His  Val Asn Met Ala Phe  Ser Gln Ser
        1100                1105                1110

Asn Pro  Pro Ser Glu Leu His  Lys Val His Gly Ser  Arg Asn Lys
        1115                1120                1125

Pro Thr  Ser Leu Trp Asn Pro  Thr Tyr Gly Ser Trp  Phe Thr Glu
        1130                1135                1140

Lys Pro  Thr Lys Lys Asn Asn  Pro Ile Ala Lys Lys  Glu Pro His
        1145                1150                1155

Asp Arg  Gly Asn Leu Gly Leu  Glu Gly Ser Cys Thr  Val Pro Pro
        1160                1165                1170

Asn Val  Ala Thr Gly Arg Leu  Pro Gly Ala Ser Leu  Leu Leu Glu
        1175                1180                1185

Pro Ser  Ser Leu Thr Ala Asn  Met Lys Glu Val Pro  Leu Phe Arg
        1190                1195                1200

Leu Arg  His Phe Pro Cys Gly  Asn Val Asn Tyr Gly  Tyr Gln Gln
        1205                1210                1215

Gln Gly  Leu Pro Leu Glu Ala  Ala Thr Ala Pro Gly  Ala Gly His
        1220                1225                1230

Tyr Glu  Asp Thr Ile Leu Lys  Ser Lys Asn Ser Met  Asn Gln Pro
        1235                1240                1245

Gly Pro
        1250

<210> SEQ ID NO 31
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
gctcctggtg cttccggcgg tacactgcag gtgggtggtc agctgcaaca tggcctggca      60
gcattccaca tttttaatg agtttaattt tgggaaaatt gacttcatgt ttttgtctcc     120
tgcctgagtg cgttcctatg gccaccactg                                     150

EML4-ALK TRANSLOCATIONS IN LUNG CANCER

CROSS-REFERENCE TO RELATED APPLICATIONS

This application is a continuation of U.S. patent application Ser. No. 15/952,424, filed Apr. 13, 2018, which is a divisional of U.S. patent application Ser. No. 14/928,347, filed Oct. 30, 2015, now U.S. Pat. No. 9,957,573, which is a continuation of U.S. patent application Ser. No. 13/518,232, filed Aug. 31, 2012, now U.S. Pat. No. 9,175,350, which is a U.S. National Stage of PCT/US2010/060858, filed Dec. 16, 2010, which claims benefit of U.S. Provisional Applications 61/289,234, filed on Dec. 22, 2009 and 61/301,551, filed Feb. 4, 2010, incorporated by reference herein in their entirety.

The instant application contains a Sequence Listing which has been submitted in ASCII format via EFS-WEB and is hereby incorporated by reference in its entirety. Said ASCII copy, created on Oct. 4, 2019, is named seqlisting.txt and is 24,078 bytes.

FIELD OF THE INVENTION

The present invention relates generally to the field of medical diagnostics. In particular, the present technology relates to methods of detecting genetic mutations associated with cancer.

BACKGROUND OF THE INVENTION

The following description is provided to assist the understanding of the reader. None of the information provided or references cited is admitted to be prior art to the present invention.

Many cancers are characterized by disruptions in cellular signaling pathways that lead to aberrant control of cellular processes, or to uncontrolled growth and proliferation of cells. These disruptions are often caused by changes in the activity of particular signaling proteins, such as kinases. Among these cancers are solid tumors, like non-small cell lung cancer (NSCLC). NSCLC is the leading cause of cancer death in the United States, and accounts for about 87% of all lung cancers. There are about 151,000 new cases of NSCLC in the United States annually, and it is estimated that over 120,000 patients will die annually from the disease in the United States alone. NSCLC, which comprises three distinct subtypes, is often only detected after it has metastasized, and thus the mortality rate is 75% within two years of diagnosis.

It is known that gene deletions and/or translocations resulting in kinase fusion proteins with aberrant signaling activity can directly lead to certain cancers. For example, it has been demonstrated that the BCR-ABL oncoprotein, a tyrosine kinase fusion protein, is a causative agent in human chronic myelogenous leukemia (CML). The BCR-ABL oncoprotein, which is found in at least 90-95% of CIVIL cases, is generated by the translocation of gene sequences from the c-ABL protein tyrosine kinase on chromosome 9 into BCR sequences on chromosome 22, producing the so-called Philadelphia chromosome. See, e.g. Kurzock et al., N. Engl. J. Med. 319: 990-998 (1988). The translocation is also observed in acute lymphocytic leukemia and NSCLC cases.

EML4-ALK is a fusion-type protein tyrosine kinase that is generated in human non-small-cell lung cancer (NSCLC) and other cancers as a result of a recurrent chromosome inversion, inv (2)(p21p23). EML4 (echinoderm microtubule-associated protein like protein 4) is a cytoplasmic protein with a molecular weight of 120,000, which is highly expressed in the M phase of the cell cycle. The human EML4 gene encodes a polypeptide with 981 amino acids and has 23 exons. The EML4 protein has a basic region at the amino terminus, as with other members of the EML family, and further has carboxyl-terminal WD domains. The function of EML4 in cells is not known. However, according to a recent report, EML4 may participate in microtubule formation.

ALK (Anaplastic Lymphoma Kinaseis receptor tyrosine kinase) is a protein that has a transmembrane domain in the central part, a carboxyl-terminal tyrosine kinase region, and an amino-terminal extracellular domain. The ALK gene has 30 exons and encodes a polypeptide with 1,620 amino acids. The ALK gene has been reported to participate in the development or functioning of the nervous system. Full-length ALK expression has been reported in some cancer cells of ectodermal origin, such as neuroblastoma, glioblastoma, breast cancer, and melanoma.

SUMMARY OF THE INVENTION

In one aspect, the present invention provides a method for diagnosing a neoplastic disorder or susceptibility to a neoplastic disorder comprising detecting the presence of a EML4-ALK gene fusion in a sample from a subject, wherein the EML4-ALK gene fusion is a fusion between exon 17 or intron 17 of EML4 and intron 19 of ALK, and diagnosing the subject as having or being susceptible to a neoplastic disorder when the gene fusion is present.

In another aspect, the invention provides a method of determining the EML4-ALK gene fusion status of a human by: (a) determining the presence or absence of the E17; ins30A20 or E17ins30; ins65A20 gene fusion in both alleles of the of the EML4-ALK fusion gene of the human in a nucleic acid sample obtained from the human, and (b) identifying the human (i) as being homozygous for E17; ins30A20 or E17ins30; ins65A20 gene fusion in the EML4-ALK fusion gene when one of the gene fusions is present in both alleles of the EML4-ALK fusion gene, or (ii) as being heterozygous for the E17; ins30A20 or E17ins30; ins65A20 gene fusion in the EML4-ALK fusion gene when one of the gene fusions is present in one of the alleles of the EML4-ALK fusion gene, or (iii) as having no alteration in the EML4-ALK fusion gene caused by the E17; ins30A20 or E17ins30; ins65A20 gene fusion when each of the gene fusions is absent from both alleles of the EML4-ALK fusion gene.

In some embodiments, the neoplastic disorder is non small cell lung cancer.

In some embodiments, the EML4-ALK gene fusion is E17; ins30A20 or E17ins30; ins65A20. An EML4-ALK gene fusion may be detected by amplifying SEQ ID NO: 1, SEQ ID NO: 2, or a diagnostic fragment thereof. In one embodiment, the method includes detecting one or more additional EML4-ALK gene fusions in a sample from the subject. For instance, the one or more additional EML4-ALK gene fusions may be selected from the group consisting of: variant 1, variant 2, variant 3a, variant 3b, variant 4, variant 5a, variant 5b, variant 6, and variant 7.

Suitable samples for assessment of EML4-ALK fusions include, for example, plasma, serum, and biopsy tissue (e.g., a lung biopsy sample).

The EML4-ALK fusion may be detected by assessing sample nucleic acid by PCR, RT-PCR, and/or nucleic acid hybridization. In one embodiment, the sample is amplified by reverse transcriptase polymerase chain reaction (RT-PCR). In one embodiment, the amplifying employs a detectably labeled primer. In one embodiment, the detecting is accomplished with electrophoresis. In one embodiment, the detecting is accomplished using a real-time PCR-based detection system, such as TaqMan®.

The present invention also provides a method for diagnosing a neoplastic disorder or susceptibility to a neoplastic disorder by detecting the presence or absence of an EML4-ALK fusion protein in a sample from a subject, wherein the EML4-ALK fusion protein is a fusion between exon 17 or intron 17 of EML4 and intron 19 of ALK, and diagnosing the subject has having or being susceptible to a neoplastic disorder when the fusion protein is present. In one embodiment, the fusion protein contains the sequence of SEQ ID NO: 29 or 30.

The invention also provides kits for detecting a EML4-ALK fusion mutations which include one or more oligonucleotides (e.g., a primer) for amplifying a fragment of a nucleic acid sample which contains the E17; ins30A20 or E17ins30; ins65A20 mutation, if present. In one embodiment, at least one of the primers contains the sequence of SEQ ID NOs: 19 and 25, or complements thereof. Optionally, the kit further contains one or more mutation-specific oligonucleotide probes. In a related aspect, the invention provides a kit containing at least one oligonucleotide having the sequence of SEQ ID NOs: 19 or 25-28, or complements thereof.

In another aspect, the invention provides an isolated polynucleotide substantially identical to SEQ ID NO: 1 or SEQ ID NO: 2 or complements thereof. Other useful a substantially purified polynucleotides include those having the sequence of any of SEQ ID NOs: 3-25 or complements thereof.

The definitions of certain terms as used in this specification are provided below. Unless defined otherwise, all technical and scientific terms used herein generally have the same meaning as commonly understood by one of ordinary skill in the art to which this invention belongs.

As used in this specification and the appended claims, the singular forms "a", "an" and "the" include plural referents unless the content clearly dictates otherwise. For example, reference to "a nucleic acid" includes a combination of two or more nucleic acids, and the like.

The term "amplification" or "amplify" as used herein means one or more methods known in the art for copying a target nucleic acid, thereby increasing the number of copies of a selected nucleic acid sequence. Amplification may be exponential or linear. A target nucleic acid may be either DNA or RNA. The sequences amplified in this manner form an "amplicon." While the exemplary methods described hereinafter relate to amplification using the polymerase chain reaction ("PCR"), numerous other methods are known in the art for amplification of nucleic acids (e.g., isothermal methods, rolling circle methods, etc.). The skilled artisan will understand that these other methods may be used either in place of, or together with, PCR methods. See, e.g., Saiki, "Amplification of Genomic DNA" in *PCR Protocols*, Innis et al., Eds., Academic Press, San Diego, Calif. 1990, pp. 13-20; Wharam et al., *Nucleic Acids Res.*, 2001, 29(11):E54-E54; Hafner et al., *Biotechniques* 2001, 30(4):852-6, 858, 860; Zhong et al., *Biotechniques,* 2001, 30(4):852-6, 858, 860.

The term "complement" as used herein means the complementary sequence to a nucleic acid according to standard Watson/Crick base pairing rules. A complement sequence can also be a sequence of RNA complementary to the DNA sequence or its complement sequence, and can also be a cDNA. The term "substantially complementary" as used herein means that two sequences hybridize under stringent hybridization conditions. The skilled artisan will understand that substantially complementary sequences need not hybridize along their entire length. In particular, substantially complementary sequences comprise a contiguous sequence of bases that do not hybridize to a target or marker sequence, positioned 3' or 5' to a contiguous sequence of bases that hybridize under stringent hybridization conditions to a target or marker sequence.

As used herein the terms "diagnose" or "diagnosis" or "diagnosing" refer to distinguishing or identifying a disease, syndrome or condition or identifying a person having a particular disease, syndrome or condition. In illustrative embodiments of the invention, assays are used to diagnose a neoplastic disorder, such as NSCLC, in a subject based on an analysis of a sample.

As used herein, the term "EML4-ALK gene fusion" refers to an aberrant gene rearrangement between the EML4 gene and the ALK gene on chromosome 2. The term EML4-ALK fusion also refers to the polypeptide formed from an inversion on human chromosome 2 in which the EML4 gene is fused to the ALK gene and that sequence is translated to form an aberrant protein. In exemplary embodiments, the EML4-ALK gene fusion is the EML4-ALK protein variant 8a or 8b, or encoding nucleic acids.

As used herein, the term "hybridize" or "specifically hybridize" refers to a process where two complementary nucleic acid strands anneal to each other under appropriately stringent conditions. Hybridizations are typically conducted with probe-length nucleic acid molecules. Nucleic acid hybridization techniques are well known in the art. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, *Molecular Cloning: A Laboratory Manual*, Second Edition, Cold Spring Harbor Press, Plainview, N.Y.; Ausubel, F. M. et al. 1994, *Current Protocols in Molecular Biology*. John Wiley & Sons, Secaucus, N.J.

By "isolated", when referring to a nucleic acid (e.g., an oligonucleotide such as RNA, DNA, or a mixed polymer) is meant a nucleic acid that is apart from a substantial portion of the genome in which it naturally occurs and/or is substantially separated from other cellular components which naturally accompany such nucleic acid. For example, any nucleic acid that has been produced synthetically (e.g., by serial base condensation) is considered to be isolated. Likewise, nucleic acids that are recombinantly expressed, cloned, produced by a primer extension reaction (e.g., PCR), or otherwise excised from a genome are also considered to be isolated.

As used herein, a "fragment" means a linear segment of a target polynucleotide that is at least about 15, 20, 25, 30, 35, 40, 45, 50, 75, 100, 200, 300, 400, 500, 1000 contiguous nucleotides or more in length.

As used herein, the term "neoplastic disorder" refers to cancers of any kind and origin and precursor stages thereof. Accordingly, the term "neoplastic disorder" includes the subject matter identified by the terms "neoplasia", "neoplasm", "cancer", "precancer" or "tumor". Neoplastic disorders to which the methods of the present invention may be applied include but are not limited to, neoplastic lesions of the respiratory tract, such as non-small cell lung cancer.

As used herein, "nucleic acid" refers broadly to segments of a chromosome, segments or portions of DNA, cDNA, and/or RNA. Nucleic acid may be derived or obtained from an originally isolated nucleic acid sample from any source (e.g., isolated from, purified from, amplified from, cloned from, or reverse transcribed from sample DNA or RNA).

As used herein, the term "oligonucleotide" refers to a short polymer composed of deoxyribonucleotides, ribonucleotides or any combination thereof. Oligonucleotides are generally between about 10 and about 100 nucleotides in length. Oligonucleotides are typically 15 to 70 nucleotides long, with 20 to 26 nucleotides being the most common. An oligonucleotide may be used as a primer or as a probe.

An oligonucleotide is "specific" for a nucleic acid if the oligonucleotide has at least 50% sequence identity with a portion of the nucleic acid when the oligonucleotide and the nucleic acid are aligned. An oligonucleotide that is specific for a nucleic acid is one that, under the appropriate hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, or at least 95% sequence identity.

As used herein, a "primer" for amplification is an oligonucleotide that specifically anneals to a target or marker nucleotide sequence. The 3' nucleotide of the primer should be identical to the target or marker sequence at a corresponding nucleotide position for optimal primer extension by a polymerase. As used herein, a "forward primer" is a primer that anneals to the anti-sense strand of double stranded DNA (dsDNA). A "reverse primer" anneals to the sense-strand of dsDNA.

As used herein, the term "sample" or "test sample" refers to any liquid or solid material containing nucleic acids. In suitable embodiments, a test sample is obtained from a biological source (i.e., a "biological sample"), such as cells in culture or a tissue sample from an animal, most preferably, a human. In an exemplary embodiment, the sample is a biopsy sample.

"Target nucleic acid" as used herein refers to segments of a chromosome, a complete gene with or without intergenic sequence, segments or portions a gene with or without intergenic sequence, or sequence of nucleic acids to which probes or primers are designed. Target nucleic acids may include wild type sequences, nucleic acid sequences containing mutations, deletions or duplications, tandem repeat regions, a gene of interest, a region of a gene of interest or any upstream or downstream region thereof. Target nucleic acids may represent alternative sequences or alleles of a particular gene. Target nucleic acids may be derived from genomic DNA, cDNA, or RNA. As used herein, target nucleic acid may be native DNA or a PCR-amplified product. In one embodiment, the target nucleic acid is a fragment of a chromosomal inversion involving a fusion of the EML4-ALK genes.

As used herein the term "stringency" is used in reference to the conditions of temperature, ionic strength, and the presence of other compounds, under which nucleic acid hybridizations are conducted. With high stringency conditions, nucleic acid base pairing will occur only between nucleic acids that have sufficiently long segments with a high frequency of complementary base sequences. Exemplary hybridization conditions are as follows. High stringency generally refers to conditions that permit hybridization of only those nucleic acid sequences that form stable hybrids in 0.018M NaCl at 65° C. High stringency conditions can be provided, for example, by hybridization in 50% formamide, 5×Denhardt's solution, 5×SSC (saline sodium citrate) 0.2% SDS (sodium dodecyl sulphate) at 42° C., followed by washing in 0.1×SSC, and 0.1% SDS at 65° C. Moderate stringency refers to conditions equivalent to hybridization in 50% formamide, 5×Denhardt's solution, 5×SSC, 0.2% SDS at 42° C., followed by washing in 0.2×SSC, 0.2% SDS, at 65° C. Low stringency refers to conditions equivalent to hybridization in 10% formamide, 5×Denhardt's solution, 6×SSC, 0.2% SDS, followed by washing in 1×SSC, 0.2% SDS, at 50° C.

As used herein the term "substantially identical" refers to a polypeptide or nucleic acid exhibiting at least 50%, 75%, 85%, 90%, 95%, or even 99% identity to a reference amino acid or nucleic acid sequence over the region of comparison. For polypeptides, the length of comparison sequences will generally be at least 20, 30, 40, or 50 amino acids or more, or the full length of the polypeptide. For nucleic acids, the length of comparison sequences will generally be at least 10, 15, 20, 25, 30, 40, 50, 75, or 100 nucleotides or more, or the full length of the nucleic acid.

As used herein, the term "patient" refers to a subject who receives medical care, attention or treatment. As used herein, the term is meant to encompass a person having or suspected of having a disease including a person who may be symptomatic for a disease but who has not yet been diagnosed.

BRIEF DESCRIPTION OF THE FIGURES

FIG. 1A is a chromatogram showing the results of amplifying RNA from FFPE tissue from a NSCLC patient using an unlableled EML4 exon 17 forward primer and FAM-labeled ALK exon 20 reverse primer. Two peaks were observed at position 171 bp and 238 bp, indicating presence of at least two fusion variants. FIG. 1B and FIG. 1C are electropherograms from reverse sequencing reactions. The 171 bp peak (FIG. 1B) consisted of a complete EML4 exon 17 and ALK exon 20 separated by 30 bp of adjacent ALK intron 19-20 sequence and the 238 bp peak (FIG. 1C) also contains a complete EML4 exon 17 and ALK exon 20 and adjacent ALK intron 19-20 with an added 4 bp (boxed) of that intron and furthermore includes 61 bp of non-adjacent intron 17-18 separating EML4 exon 17 and ALK intron sequence.

DETAILED DESCRIPTION

Figure 2A:
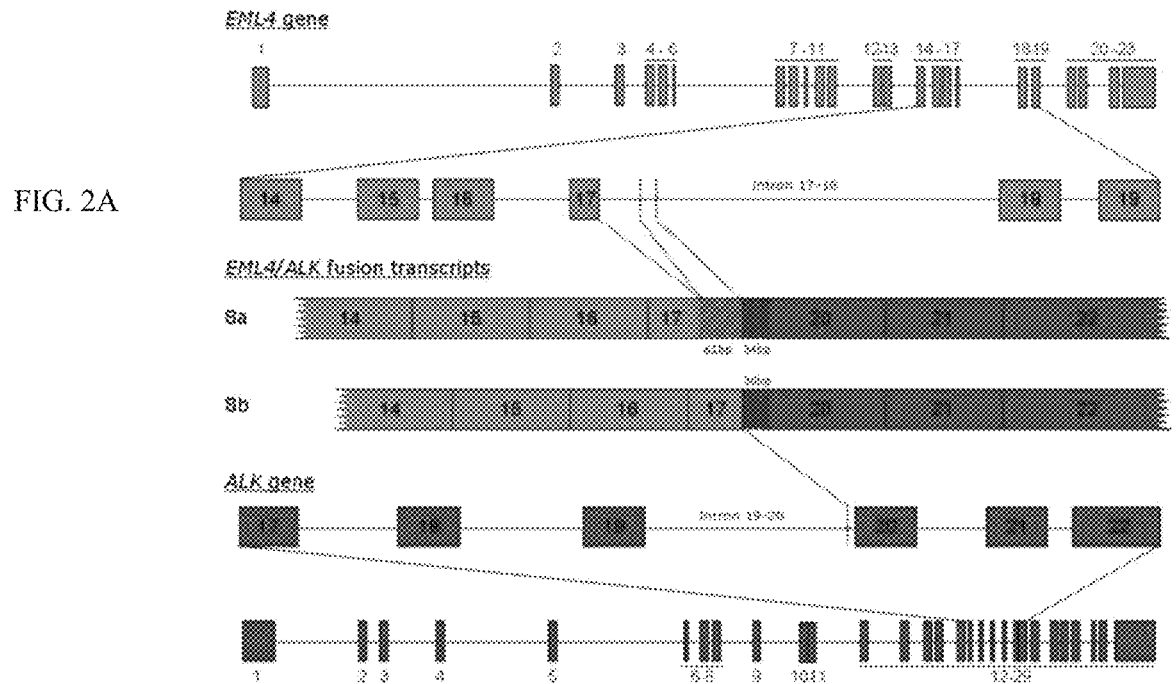
FIG. 2A and FIG. 2B are schematic diagrams of fusion transcripts resulting from EML4 (light) and ALK (dark) genetic rearrangement of the EML4-ALK variants 8a and 8b, respectively. Intronic sequences carried over to the fusion transcripts are indicated by dotted lines. Putative EML4 truncation containing the N-terminal region of EML4 consisting of HELP and partial WD repeat domains (variant 8a) and fusion of the N-terminal region of EML4 to the C-terminal region of ALK containing the protein tyrosine kinase domain (variant 8b). Breakpoints indicated with a dotted line. IDS, intron-derived sequence; TM, transmembrane domain.

In accordance with the present invention, methods are provided for detecting a particular nucleic acid segment of interest in a sample of nucleic acids. In particular embodiments, the nucleic acid segment of interest includes the junction of a fusion of the EML4-ALK genes. This information may be used to determine if an individual is suffering from or is susceptible to a neoplastic disorder, such as NSCLC.

In practicing the methods described herein, many conventional techniques in molecular biology, protein biochemistry, cell biology, immunology, microbiology and recombinant DNA are used. These techniques are well-known and are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, NY, 1989); *DNA Cloning: A Practical Approach*, Vols. I and II, Glover, Ed. (1985); *Oligonucleotide Synthesis*, Gait, Ed. (1984); *Nucleic Acid Hybridization*, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, *Meth. Enzymol.*, (Academic Press, Inc., 1984); *Gene Transfer Vectors for Mammalian Cells*, Miller & Calos, Eds. (Cold Spring Harbor Laboratory, NY, 1987); and *Meth. Enzymol.*, Vols. 154 and 155, Wu & Grossman, and Wu, Eds., respectively.

Assays for the Detection of EML4-ALK Fusion Genes

In one aspect, the present methods are designed to detect various target nucleic acids associated with cancer, e.g., non-small cell lung cancer. In one embodiment, an assay for an EML4-ALK gene fusion involves detecting nucleic acid segments corresponding to the fusion gene that are relevant to a diagnosis of cancer. Nucleic acid segments may be detected in a variety of ways, which are described in further detail below. In one embodiment, an assay for EML4-ALK gene fusions may be performed using PCR or RT-PCR. In another embodiment, an assay for an EML4-ALK gene fusion involves detecting an aberrant protein.

In one embodiment, the EML4-ALK variant (designated "variant 8a") is a fusion between exon 20 of ALK and exon 17 of EML4 with an insertion of 30 nucleotides of ALK introns 19-20. According to the nomenclature of Horn and Pao, *J Clin Oncol* 27: 4232-4235 (2009), this variant would be named "E17; ins30A20". The sequence of variant 8a surrounding the breakpoint is set forth in SEQ ID NO: 1. Nucleotides 1-24 of SEQ ID NO: 1 represent the 3'-region of ALK exon 20. Nucleotides 55-78 of SEQ ID NO: 1 represent the 5'-region of EML4 exon 17. The underlined region (nucleotides 25-54) of SEQ ID NO: 1 is the 30 nucleotide insert from ALK introns 19-20.

```
                                        (SEQ ID NO: 1)
GCTCCTGGTG CTTCCGGCGG TACACTGCAG GTGGGTGGTC
AGCTGCAACA TGGCCTGCCT GAGTGCGTTC CTATGGCC
```

Thus, variant 8a may be detected by detecting the presence of the 5' insertion junction (CGGCGGTACA:CTGCAGGTGG; SEQ ID NO: 26), the 3'-insertion junction (GCAACATGGC:CTGCCTGAGT; SEQ ID NO: 27), or the entire insertion (underlined), wherein the colon indicates the junction between the intron 19-20 insertion and the exonic sequences. The presence of the 5'- and 3'-junctions (e.g., SEQ ID NOs: 26 and 27) or the full ALK intron 19-20 insertion may be assessed by any convenient method including nucleotide sequence and/or hybridization of an oligonucleotide probe that contains a sufficient number of nucleotides on either side of the junction in order that specific hybridization can be assessed. The simultaneous presence of both the 5'- and 3'-junctions (SEQ ID NOs: 26 and 27) in a single sample, or the ALK intron 19-20 insert alone (e.g., in mRNA) are indicative of variant 8a EML4-ALK translocation. The exemplary 20-mer sequences provided above, or complements thereof, may be used hybridization probes or otherwise may be used as target regions of interest for assessment of variant 8a.

In one embodiment, an EML4-ALK variant (designated "variant 8b") is a fusion between exon 20 of ALK and exon 17 of EML4 with an insertion of 95 nucleotides between the ALK and EML4 exons. The insertion sequence, in the 5'-to-3' direction consists of the same 30 nucleotides from ALK introns 19-20 as in variant 8a, a four nucleotide insert (CTGG), and 61 nucleotides from EML4 introns 17-18. According to the nomenclature of Horn and Pao, this variant would be named "E17ins30; ins65A20". The sequence of variant 8b surrounding the breakpoint is set forth in SEQ ID NO: 2. Nucleotides 1-24 of SEQ ID NO: 2 represent the 3'-region of ALK exon 20. Nucleotides 120-143 of SEQ ID NO: 2 represent the 5'-region of EML4 exon 17. The underlined region (nucleotides 25-54) of SEQ ID NO: 2 is the 30 nucleotide insert from ALK introns 19-20. The lower case nucleotides (nucleotides 55-58) is the four base insert. And, the bold, italicized nucleotides (nucleotides 59-119) is the inserted sequence from EML4 introns 17-18.

```
                                        (SEQ ID NO: 2)
GCTCCTGGTG CTTCCGGCGG TACACTGCAG GTGGGTGGTC

AGCTGCAACA TGGCctggCA GCATTCCACA TTTTTTAATG

AGTTTAATTT TGGGAAAATT GACTTCATGT TTTTGTCTCC

TGCCTGAGTG CGTTCCTATG GCC
```

Thus, variant 8b may be detected by detecting the present of the 5' insertion junction (e.g., SEQ ID NO: 26), the 3'-insertion junction (TTTTTGTCTC:CTGCCTGAGT; SEQ ID NO: 28), or the entire 95 bp insertion, wherein the colon indicates the junction between the intronic insertions and the exonic sequences. The presence of the 5'- and 3'-junctions (e.g., SEQ ID NOs: 26 and 28) or the full 95 bp insertion (or a diagnostic portion thereof) may be assessed by any convenient method including nucleotide sequence and/or hybridization of an oligonucleotide probe that contains a sufficient number of nucleotides on either side of the junction in order that specific hybridization can be assessed. The simultaneous presence of both the 5'- and 3'-junctions (SEQ ID NOs: 26 and 28) in a single sample, or the full 95 bp insertion (or a diagnostic portion thereof) (e.g., in mRNA) are indicative of variant 8b EML4-ALK translocation. The exemplary 20-mer sequences provided above, or complements thereof, may be used hybridization probes or otherwise may be used as target regions of interest for assessment of variant 8b.

In one aspect, the methods may detect two or more EML-ALK gene fusion variants, e.g., in a multiplex or multiple singleplex PCR assays. For instance the assay may detect variant 8a and/or variant 8b with one or more of the following variants: variant 1, variant 2, variant 3a, variant 3b, variant 4, variant 5a, variant 5b, variant 6, and variant 6. A description of these variants is set forth in Table 1, and are described further in Horn and Pao, *J Clin Oncol* 27: 4232-4235 (2009).

TABLE 1

EML4-ALK Fusion Variants

| Variant | Description |
| --- | --- |
| V1 (E13; A20) | Variant 1 fuses exon 13 of EML4 to exon 20 of ALK. |
| V2 (E20; A20) | Variant 2 fuses exon 20 of EML4 to exon 20 of ALK. |
| V3a (E6a; A20) | Variant 3a fuses exon 6a of EML4 to exon 20 of ALK. |
| V3b (E6b; A20) | Variant 3b fuses exon 6b of EML4 to exon 20 of ALK. |
| V4 (E14; ins11del49A20) | Variant 4 fuses exon 14 of EML4 with an additional 11 nucleotides of unknown origin to nucleotide 50 within exon 20 ALK. |
| V5a (E2; A20) | Variant 5a fuses exon 2 of EML4 to exon 20 of ALK. |
| V5b (E2; ins117A20) | Variant 5b fuses exon 2 of EML4 to intron 19 of ALK (including 117 nucleotides from intron 19). |
| V6 (E13; ins69A20) | Variant 6 fuses exon 13 of EML4 to intron 19 of ALK (including 69 nucleotides from intron 19). |
| V7 (E14; del12A20) | Variant 7 fuses exon 13 of EML4 to nucleotide 13 in within exon 20 of ALK. |
| V8a (E17; ins30A20) | Variant 8a fuses exon 17 of EML4 to intron 19 of ALK (including 35 nucleotides from intron 19). |
| V8b (E17ins30; ins65A20) | Variant 8b fuses exon 17 (with an addition 60 nucleotides from intron 18) of EML4 to intron 19 of ALK (including 35 nucleotides from intron 19). |

Exemplary RT-PCR primers for the detection of EML-ALK fusions are shown in Table 2 below. With regard to the exemplary primers and probes, those skilled in the art will readily recognize that nucleic acid molecules may be double-stranded molecules and that reference to a particular site on one strand refers, as well, to the corresponding site on a complementary strand. In defining a variant position, allele, or nucleotide sequence, reference to an adenine, a thymine (uridine), a cytosine, or a guanine at a particular site on one strand of a nucleic acid molecule also defines the thymine (uridine), adenine, guanine, or cytosine (respectively) at the corresponding site on a complementary strand of the nucleic acid molecule. Thus, reference may be made to either strand in order to refer to a particular variant position, allele, or nucleotide sequence. Probes and primers, may be designed to hybridize to either strand and detection methods disclosed herein may generally target either strand.

Sample Collection and Preparation

The methods and compositions of this invention may be used to detect nucleic acids associated with various EML4-ALK gene fusions using a biological sample obtained from an individual. The nucleic acid (DNA or RNA) may be isolated from the sample according to any methods well known to those of skill in the art. Biological samples may be obtained by standard procedures and may be used immediately or stored, under conditions appropriate for the type of biological sample, for later use.

Starting material for the detection assays is typically a clinical sample, which is suspected to contain the target nucleic acids. An example of a clinical sample is a tissue from a biopsy. Next, the nucleic acids may be separated from proteins and sugars present in the original sample. Any purification methods known in the art may be used in the context of the present invention. Nucleic acid sequences in the sample can successfully be amplified using in vitro amplification, such as PCR. Typically, any compounds that may inhibit polymerases are removed from the nucleic acids.

Methods of obtaining test samples are well known to those of skill in the art and include, but are not limited to, aspirations, tissue sections, swabs, drawing of blood or other fluids, surgical or needle biopsies, and the like. The test sample may be obtained from an individual or patient. The test sample may contain cells, tissues or fluid obtained from a patient suspected being afflicted with or cancer, e.g., NSCLC. The test sample may be a cell-containing liquid or a tissue. Samples may include, but are not limited to, cells from a vaginal swab, amniotic fluid, biopsies, blood, blood cells, bone marrow, fine needle biopsy samples, peritoneal fluid, amniotic fluid, plasma, pleural fluid, saliva, semen, serum, tissue or tissue homogenates, frozen or paraffin sections of tissue. Samples may also be processed, such as sectioning of tissues, fractionation, purification, or cellular organelle separation.

If necessary, the sample may be collected or concentrated by centrifugation and the like. The cells of the sample may be subjected to lysis, such as by treatments with enzymes, heat, surfactants, ultrasonication, or a combination thereof. The lysis treatment is performed in order to obtain a sufficient amount of nucleic acid derived from the cells in the sample to detect using polymerase chain reaction.

Nucleic Acid Extraction and Amplification

The nucleic acid to be amplified may be from a biological sample such as a tissue sample and the like. Various methods of extraction are suitable for isolating the DNA or RNA. Suitable methods include phenol and chloroform extraction. See Maniatis et al., *Molecular Cloning, A Laboratory Manual*, 2d, Cold Spring Harbor Laboratory Press, pp. 16-54 (1989). Numerous commercial kits also yield suitable DNA and RNA including, but not limited to, QIAamp™ mini blood kit, Agencourt Genfind™, Roche Cobas® Roche MagNA Pure® or phenol:chloroform extraction using Eppendorf Phase Lock Gels®, and the NucliSens extraction kit (Biomerieux, Marcy l'Etoile, France).

Nucleic acid extracted from cells or tissues can be amplified using nucleic acid amplification techniques well know in the art. By way of example, but not by way of limitation, these techniques can include the polymerase chain reaction (PCR), reverse transcriptase polymerase chain reaction (RT-PCR), nested PCR, ligase chain reaction. See Abravaya, K., et al., *Nucleic Acids Research*, 23:675-682, (1995), branched DNA signal amplification, Urdea, M. S., et al., *AIDS*, 7 (suppl 2):S11-S 14, (1993), amplifiable RNA reporters, Q-beta replication, transcription-based amplification, boomerang DNA amplification, strand displacement activation, cycling probe technology, isothermal nucleic acid sequence based amplification (NASBA). See Kievits, T. et al., *J Virological Methods*, 35:273-286, (1991), Invader Technology, or other sequence replication assays or signal amplification assays may also be used. These methods of amplification are each described briefly below and are well-known in the art.

Some methods employ reverse transcription of RNA to cDNA. The method of reverse transcription and amplification may be performed by previously published or recommended procedures. Various reverse transcriptases may be used, including, but not limited to, MMLV RT, RNase H mutants of MMLV RT such as Superscript and Superscript II (Life Technologies, GIBCO BRL, Gaithersburg, Md.), AMV RT, and thermostable reverse transcriptase from *Thermus thermophilus*. For example, one method which may be used to convert RNA to cDNA is the protocol adapted from the Superscript II Preamplification system (Life Technologies, GIBCO BRL, Gaithersburg, Md.; catalog no. 18089-011), as described by Rashtchian, A., *PCR Methods Applic.*, 4:S83-S91, (1994).

LCR is a method of DNA amplification similar to PCR, except that it uses four primers instead of two and uses the enzyme ligase to ligate or join two segments of DNA. LCR can be performed as according to Moore et al., *J Clin Micro*, 36(4):1028-1031 (1998). Briefly, an LCR reaction mixture contains two pair of primers, dNTP, DNA ligase and DNA polymerase representing about 90 µl, to which is added 100 µl of isolated nucleic acid from the target organism. Amplification is performed in a thermal cycler (e.g., LCx of Abbott Labs, Chicago, Ill.).

TAS is a system of nucleic acid amplification in which each cycle is comprised of a cDNA synthesis step and an RNA transcription step. In the cDNA synthesis step, a sequence recognized by a DNA-dependent RNA polymerase (i.e., a polymerase-binding sequence or PBS) is inserted into the cDNA copy downstream of the target or marker sequence to be amplified using a two-domain oligonucleotide primer. In the second step, an RNA polymerase is used to synthesize multiple copies of RNA from the cDNA template. Amplification using TAS requires only a few cycles because DNA-dependent RNA transcription can result in 10-1000 copies for each copy of cDNA template. TAS can be performed according to Kwoh et al., *PNAS*, 86:1173-7 (1989). Briefly, extracted RNA is combined with TAS amplification buffer and bovine serum albumin, dNTPs, NTPs, and two oligonucleotide primers, one of which contains a PBS. The sample is heated to denature the RNA template and cooled to the primer annealing temperature. Reverse transcriptase (RT) is added the sample incubated at the appropriate temperature to allow cDNA elongation. Subsequently T7 RNA polymerase is added and the sample is incubated at 37° C. for approximately 25 min for the synthesis of RNA. The above steps are then repeated. Alternatively, after the initial cDNA synthesis, both RT and RNA polymerase are added following a 1 min 100° C. denaturation followed by an RNA elongation of approximately 30 min at 37° C. TAS can be also be performed on solid phase as according to Wylie et al., *J Clin Micro*, 36(12):3488-3491 (1998). In this method, nucleic acid targets are captured with magnetic beads containing specific capture primers. The beads with captured targets are washed and pelleted before adding amplification reagents which contains amplification primers, dNTP, NTP, 2500 U of reverse transcriptase and 2500 U of T7 RNA polymerase. A 100 µl TMA reaction mixture is placed in a tube, 200 µl oil reagent is added and amplification is accomplished by incubation at 42° C. in a waterbath for one hour.

NASBA is a transcription-based amplification method which amplifies RNA from either an RNA or DNA target. NASBA is a method used for the continuous amplification of nucleic acids in a single mixture at one temperature. For example, for RNA amplification, avian myeloblastosis virus (AMV) reverse transcriptase, RNase H and T7 RNA polymerase are used. This method can be performed as according to Heim, et al., *Nucleic Acids Res.*, 26(9):2250-2251 (1998). Briefly, an NASBA reaction mixture contains two specific primers, dNTP, NTP, 6.4 U of AMV reverse transcriptase, 0.08 U of *E. coli* Rnase H, and 32 U of T7 RNA polymerase. The amplification is carried out for 120 min at 41° C. in a total volume of 20 µl.

In a related method, self-sustained sequence-replication (3 SR) reaction, isothermal amplification of target DNA or RNA sequences in vitro using three enzymatic activities: reverse transcriptase, DNA-dependent RNA polymerase and *E. coli* ribonuclease H. This method may be modified from a 3-enzyme system to a 2-enzyme system by using human immunodeficiency virus (HIV)-1 reverse transcriptase instead of avian myeloblastosis virus (AMV) reverse transcriptase to allow amplification with T7 RNA polymerase but without *E. coli* ribonuclease H. In the 2-enzyme 3 SR, the amplified RNA is obtained in a purer form compared with the 3-enzyme 3 SR (Gebinoga & Oehlenschlager *Eur J Biochem*, 235:256-261, 1996).

SDA is an isothermal nucleic acid amplification method. A primer containing a restriction site is annealed to the template. Amplification primers are then annealed to 5' adjacent sequences (forming a nick) and amplification is started at a fixed temperature. Newly synthesized DNA strands are nicked by a restriction enzyme and the polymerase amplification begins again, displacing the newly synthesized strands. SDA can be performed as according to Walker, et al., *PNAS*, 89:392-6 (1992). Briefly, an SDA reaction mixture contains four SDA primers, dGTP, dCTP, TTP, dATP, 150 U of Hinc II, and 5 U of exonuclease-deficient of the large fragment of *E. coli* DNA polymerase I (exo⁻ Klenow polymerase). The sample mixture is heated 95° C. for 4 min to denature target DNA prior to addition of the enzymes. After addition of the two enzymes, amplification is carried out for 120 min at 37° C. in a total volume of 50 µl. Then, the reaction is terminated by heating for 2 min at 95° C.

The Q-beta replication system uses RNA as a template. Q-beta replicase synthesizes the single-stranded RNA genome of the coliphage Qβ. Cleaving the RNA and ligating in a nucleic acid of interest allows the replication of that sequence when the RNA is replicated by Q-beta replicase (Kramer & Lizardi, *Trends Biotechnol.*, 1991 9(2):53-8, 1991).

In suitable embodiments, PCR is used to amplify a target sequence of interest. PCR is a technique for making many copies of a specific template DNA sequence. The reaction consists of multiple amplification cycles and is initiated using a pair of primer sequences that hybridize to the 5' and 3' ends of the sequence to be copied. The amplification cycle includes an initial denaturation, and typically up to 50 cycles of annealing, strand elongation and strand separation (denaturation). In each cycle of the reaction, the DNA sequence between the primers is copied. Primers can bind to the copied DNA as well as the original template sequence, so the total number of copies increases exponentially with time. PCR can be performed as according to Whelan et al., *J of Clin Micro*, 33(3):556-561 (1995). Briefly, a PCR reaction mixture includes two specific primers, dNTPs, approximately 0.25 U of Taq polymerase, and 1×PCR Buffer.

The skilled artisan is capable of designing and preparing primers that are appropriate for amplifying a target or marker sequence. The length of the amplification primers depends on several factors including the nucleotide sequence identity and the temperature at which these nucleic acids are hybridized or used during in vitro nucleic acid amplification. The considerations necessary to determine a preferred length for an amplification primer of a particular sequence identity are well-known to a person of ordinary skill. For example, the length of a short nucleic acid or oligonucleotide can relate to its hybridization specificity or selectivity. Exemplary primers for detecting EML4-ALK gene fusion by RT-PLR are set forth in Table 2.

In some embodiments, the amplification may include a labeled primer or probe, thereby allowing detection of the amplification products corresponding to that primer or probe. In particular embodiments, the amplification may include a multiplicity of labeled primers or probes; such primers may be distinguishably labeled, allowing the simultaneous detection of multiple amplification products.

In one embodiment, a primer or probe is labeled with a fluorogenic reporter dye that emits a detectable signal. While a suitable reporter dye is a fluorescent dye, any reporter dye that can be attached to a detection reagent such as an oligonucleotide probe or primer is suitable for use in the invention. Such dyes include, but are not limited to, Acridine, AMCA, BODIPY, Cascade Blue, Cy2, Cy3, Cy5, Cy7, Edans, Eosin, Erythrosin, Fluorescein, 6-Fam, Tet, Joe, Hex, Oregon Green, Rhodamine, Rhodol Green, Tamra, Rox, and Texas Red.

In yet another embodiment, the detection reagent may be further labeled with a quencher dye such as Tamra, Dabcyl, or Black Hole Quencher® (BHQ), especially when the reagent is used as a self-quenching probe such as a TaqMan® (U.S. Pat. Nos. 5,210,015 and 5,538,848) or Molecular Beacon probe (U.S. Pat. Nos. 5,118,801 and 5,312,728), or other stemless or linear beacon probe (Livak et al., 1995, PCR Method Appl., 4:357-362; Tyagi et al, 1996, Nature Biotechnology, 14:303-308; Nazarenko et al., 1997, Nucl. Acids Res., 25:2516-2521; U.S. Pat. Nos. 5,866,336 and 6,117,635).

Nucleic acids may be amplified prior to detection or may be detected directly during an amplification step (i.e., "real-time" methods). In some embodiments, the target sequence is amplified using a labeled primer such that the resulting amplicon is detectably labeled. In some embodiments, the primer is fluorescently labeled. In some embodiments, the target sequence is amplified and the resulting amplicon is detected by electrophoresis.

In one embodiment, detection of a target nucleic acid, such as a nucleic acid from an EML4-ALK gene fusion, is performed using the TaqMan® assay, which is also known as the 5' nuclease assay (U.S. Pat. Nos. 5,210,015 and 5,538,848). The TaqMan® assay detects the accumulation of a specific amplified product during PCR. The TaqMan® assay utilizes an oligonucleotide probe labeled with a fluorescent reporter dye and a quencher dye. The reporter dye is excited by irradiation at an appropriate wavelength, it transfers energy to the quencher dye in the same probe via a process called fluorescence resonance energy transfer (FRET). When attached to the probe, the excited reporter dye does not emit a signal. The proximity of the quencher dye to the reporter dye in the intact probe maintains a reduced fluorescence for the reporter. The reporter dye and quencher dye may be at the 5' most and the 3' most ends, respectively or vice versa. Alternatively, the reporter dye may be at the 5' or 3' most end while the quencher dye is attached to an internal nucleotide, or vice versa. In yet another embodiment, both the reporter and the quencher may be attached to internal nucleotides at a distance from each other such that fluorescence of the reporter is reduced.

During PCR, the 5' nuclease activity of DNA polymerase cleaves the probe, thereby separating the reporter dye and the quencher dye and resulting in increased fluorescence of the reporter. Accumulation of PCR product is detected directly by monitoring the increase in fluorescence of the reporter dye. The DNA polymerase cleaves the probe between the reporter dye and the quencher dye only if the probe hybridizes to the target-containing template which is amplified during PCR.

TaqMan® primer and probe sequences can readily be determined using the variant and associated nucleic acid sequence information provided herein. A number of computer programs, such as Primer Express (Applied Biosystems, Foster City, Calif.), can be used to rapidly obtain optimal primer/probe sets. It will be apparent to one of skill in the art that such primers and probes for detecting the target nucleic acids are useful in diagnostic assays for neoplastic disorders, such as NSCLC, and can be readily incorporated into a kit format. The present invention also includes modifications of the TaqMan® assay well known in the art such as the use of Molecular Beacon probes (U.S. Pat. Nos. 5,118,801 and 5,312,728) and other variant formats (U.S. Pat. Nos. 5,866,336 and 6,117,635).

In an illustrative embodiment, real time PCR is performed using TaqMan® probes in combination with a suitable amplification/analyzer such as the ABI Prism® 7900HT Sequence Detection System. The ABI PRISM® 7900HT Sequence Detection System is a high-throughput real-time PCR system that detects and quantitates nucleic acid sequences. Real time detection on the ABI Prism 7900HT or 7900HT Sequence Detector monitors fluorescence and calculates Rn during each PCR cycle. The threshold cycle, or Ct value, is the cycle at which fluorescence intersects the threshold value. The threshold value is determined by the sequence detection system software or manually. The Ct can be correlated to the initial amount of nucleic acids or number of starting cells using a standard curve.

Other methods of probe hybridization detected in real time can be used for detecting amplification of a target or marker sequence flanking a tandem repeat region. For example, the commercially available MGB Eclipse™ probes (Epoch Biosciences), which do not rely on a probe degradation can be used. MGB Eclipse™ probes work by a hybridization-triggered fluorescence mechanism. MGB Eclipse™ probes have the Eclipse™ Dark Quencher and the MGB positioned at the 5'-end of the probe. The fluorophore is located on the 3'-end of the probe. When the probe is in solution and not hybridized, the three dimensional conformation brings the quencher into close proximity of the fluorophore, and the fluorescence is quenched. However, when the probe anneals to a target or marker sequence, the probe is unfolded, the quencher is moved from the fluorophore, and the resultant fluorescence can be detected.

Oligonucleotide probes can be designed which are between about 10 and about 100 nucleotides in length and hybridize to the amplified region. Oligonucleotides probes are preferably 12 to 70 nucleotides; more preferably 15-60 nucleotides in length; and most preferably 15-25 nucleotides in length. The probe may be labeled. Amplified fragments may be detected using standard gel electrophoresis methods. For example, in some embodiments, amplified fractions are separated on an agarose gel and stained with ethidium bromide by methods known in the art to detect amplified fragments.

As a quality control measure, an internal amplification control may be included in one or more samples to be extracted and amplified. The skilled artisan will understand that any detectable sequence that is not typically present in the sample can be used as the control sequence. A control sequence can be produced synthetically. If PCR amplification is successful, the internal amplification control amplicons can then be detected. Additionally, if included in the sample prior to purification of nucleic acids, the control sequences can also act as a positive purification control.

Protein Assays

In one aspect, the present invention provides methods of detecting a mutant protein associated with a neoplastic disorder, such as NSCLC. In one embodiment, the methods provide for detection of an EML4-ALK fusion protein. The presence of EML4-ALK fusion proteins can be measured by immunoassay, using antibodies specific for the mutant protein. Lack of antibody binding would indicate the absence of mutant EML4-ALK molecules and suggest that the subject does not have or is not susceptible to a neoplastic disorder associated with the mutant EML4-ALK protein. Antibodies specific to wild-type EML4 or ALK protein may be used as a control.

Antibodies which are specifically reactive with mutant EML4-ALK proteins may be obtained in a number of ways which will be readily apparent to those skilled in the art. The fusion protein can be produced in a recombinant system using the mutant nucleotide sequence. The recombinant protein can be injected into an animal as an immunogen to elicit polyclonal antibody production. The resultant polyclonal antisera may be used directly or may be purified by, for example, affinity absorption using recombinantly produced EML4-ALK fusion proteins coupled to an insoluble support.

In another alternative, monoclonal antibodies specifically immunoreactive with the fusion protein may be prepared according to well known methods (See, e.g., Kohler and Milstein, 1976, *Eur. J. Immunol.*, 6:611), using a peptide as an immunogen, using it for selection or using it for both functions. These and other methods for preparing antibodies that are specifically immunoreactive with the recombinant protein of this invention are easily within the skill of the ordinary worker in the art. Suitably, antibodies specific for mutant EML4-ALK fusion protein will not react with normal (wild type) EML4 or ALK proteins. Similar methods can be used to produce antibodies specifically immunoreactive with wild-type EML4 or ALK.

Kits

In a further aspect, the invention disclosure provides kits for diagnosing a neoplastic disorder in an individual, the kit comprising: a set of reagents for determining the presence or absence, or differential presence, of EML4-ALK gene fusions. In one embodiment, at least one primer pair is selected from the group consisting of: SEQ ID NOs: 3/25, 4/25, 5/25, 6/25, 7/25, 8/25, 9/25, 10/25, 11/25, 12/25, 13/25; 16/25, 17/25, 18/25, 19/25, 20/25, 21/25, 22/25, 23/25, and 24/25. In one embodiment, the kit contains one or more of the primers of SEQ ID NOs: 3-28.

EXAMPLE

The present invention is further illustrated by the following examples, which should not be construed as limiting in any way.

Example 1

Cytogenetic Analysis

FFPE sections 4-5 μm in size were used for FISH with an ALK dual-color break-apart probe (Abbott Molecular, Inc., Des Plaines, Ill.); the slides were deparaffinized prior to probe application. FISH analysis was performed using a Nikon 50i fluorescence microscope (Nikon Corp., Tokyo, Japan). The images were captured using a CCD camera and Isis® imaging system (MetaSystems Group, Inc., Watertown, Mass.). Unstained slides were deparaffinized and stained with CONFIRM™ anti-ALK1 primary antibody (mouse monoclonal clone ALK01; Ventana Medical Systems, Tucson Ariz.). All immunohistochemistry steps were performed using the BenchMark XT, according to manufacturer's protocol (Ventana Medical Systems, Tucson, Ariz.).

Cytogenetic analysis of a non-small cell lung cancer (NSCLC) patient revealed breakage within the ALK gene. Both haploid and diploid cells were observed where split signal from the 5' and 3' ALK probes were evident. Likewise, immunohistochemistry of the tissue sample confirmed significant ALK1 staining indicating overexpression of ALK1 in the malignant cells.

Example 2

Evaluation of EML4-ALK Fusions

Because the FISH and IHC results from Example 1 indicated an oncogenic ALK1 rearrangement, the molecular characteristics were further investigated under the assumption that there was an EML4-ALK fusion event. RT-PCR amplification with primers to detect the first 11 published EML4-ALK fusion variants (variant 1, 2, 3a, 3b, 4, 5a, 5b, 6, and 7) yielded results that suggested the likely involvement of a previously undescribed EML4-ALK fusion variant(s).

Methods. Sixty (60) patient samples were analyzed with the multiplex assay: 55 formalin-fixed paraffin-embedded (FFPE) NSCLC samples (37 patients with adenocarcinoma, 11 squamous cell carcinoma, 5 adenosquamous cell carcinoma and 2 large cell carcinomas), 4 cell line samples (3 NSCLC; 1 Prostate Cancer), and 1 control RNA (Human Total RNA, Applied Biosystems). Tissue blocks were sectioned onto slides for H&E staining or unstained for RNA extraction. Tumor area was identified by a licensed pathologist and tissue from this area was scraped for RNA extraction with HighPure miRNA Isolation kit (Roche Applied Science, Mannheim, Germany). RNA was DNase I digested with DNA-free (Applied Biosystems/Ambion, Austin Tex.) prior to amplification.

After RNA extraction, RT-PCR was performed using the RNA UltraSense™ One-Step qRT-PCR System (Invitrogen, Carlsbad, Caif.). 23 primers (22 unlabeled EML4 forward; 1 FAM labeled ALK reverse) were included in 4 master mixes to amplify EML4-ALK fusions initiating within the first 22 EML4 exons to ALK exon 20 (Table 2). One endogenous control (beta-2-microglobulin) primer set was included in a separate reaction. Thermocycling was performed as follows: RNA reverse transcribed by incubation at 55° C. for 30 min followed by denaturing step at 94° C. for 2 min; PCR amplification performed by 40 cycles of denaturation at 94° C. for 15 sec; annealing at 60° C. for 30 min; extension at 68° C.; and final extension at 68° C. for 5 min following cycling. RT-PCR to query alternative splicing in intron 17 was performed as above, with exception that the annealing temperature was 50° C. Exemplary primers include:

TABLE 2

Exemplary RT-PCR Primers for Detecting EML4-ALK Gene Fusions

| Primer Target | Sequence (5' to 3') | SEQ ID NO: |
|---|---|---|
| EML4 Exon 1 (Forward) | CGGTCCGCTGAATGAAGT | SEQ ID NO: 3 |
| EML4 Exon 2 (Forward) | AAGATCATGTGGCCTCAGTG | SEQ ID NO: 4 |
| EML4 Exon 3 (Forward) | TGGTGCAAACAGAAAACCAA | SEQ ID NO: 5 |

TABLE 2-continued

Exemplary RT-PCR Primers for Detecting EML4-ALK Gene Fusions

| Primer Target | Sequence (5' to 3') | SEQ ID NO: |
|---|---|---|
| EML4 Exon 4 (Forward) | CCCTCTTCACAACCTCTCCA | SEQ ID NO: 6 |
| EML4 Exon 5 (Forward) | ACGACCATCACCAGCTGAAA | SEQ ID NO: 7 |
| EML4 Exon 6 (Forward) | CTGCAGACAAGCATAAAGATG | SEQ ID NO: 8 |
| EML4 Exon 7 (Forward) | GTCGGCCAATTACCATGTTC | SEQ ID NO: 9 |
| EML4 Exon 8 (Forward) | CTTCCGACCGGGAAAATAGT | SEQ ID NO: 10 |
| EML4 Exon 9 (Forward) | ACATCCTGACAAAATTAGGATTGC | SEQ ID NO: 11 |
| EML4 Exon 10 (Forward) | CCTCTACAACCCCACGTCAG | SEQ ID NO: 12 |
| EML4 Exon 11 (Forward) | GCATATGCTTACTGTATGGGACTG | SEQ ID NO: 13 |
| EML4 Exon 12 (Forward) | TTTCACCCAACAGATGCAAA | SEQ ID NO: 14 |
| EML4 Exon 13 (Forward) | GACTCAGGTGGAGTCATGC | SEQ ID NO: 15 |
| EML4 Exon 14 (Forward) | AAGCTCATGATGGCAGTGTG | SEQ ID NO: 16 |
| EML4 Exon 15 (Forward) | TGTAGCAGAAGGAAAGGCAGA | SEQ ID NO: 17 |
| EML4 Exon 16 (Forward) | GTCTTGCCACACATCCCTTC | SEQ ID NO: 18 |
| EML4 Exon 17 (Forward) | CCAGGACACTGTGCAGATTT | SEQ ID NO: 19 |
| EML4 Exon 18 (Forward) | AGGTGGTTTGTTCTGGATGC | SEQ ID NO: 20 |
| EML4 Exon 19 (Forward) | CCTTCCTGGCTGTAGGATCTC | SEQ ID NO: 21 |
| EML4 Exon 20 (Forward) | CAGATATGGAAGGTGCACTG | SEQ ID NO: 22 |
| EML4 Exon 21 (Forward) | ATTCCAAATGGCTGCAAACT | SEQ ID NO: 23 |
| EML4 Exon 22 (Forward) | AGCTGTTGCCGATGACTTTT | SEQ ID NO: 24 |
| ALK Exon 20 (Reverse) | AGCTTGCTCAGCTTGTACTC | SEQ ID NO: 25 |

RT-PCR products were diluted 1:10 with $H_2O$, denatured in formamide containing ROX GeneScan 350 size marker (Applied Biosystems, Foster City Calif.), and size fractionated by capillary electrophoresis in an ABI 3730 Genetic Analyzer (Applied Biosystems, Foster City Calif.). Results were analyzed by GeneMapper Software (Applied Biosystems, Foster City Calif.). Samples with positive results were further analyzed by singleplex RT-PCR to confirm exon involvement and novel fusions were confirmed by direct sequencing.

For cDNA sequencing, RT-PCR products were separated by capillary electrophoresis on a 2% agarose gel. Individual bands were cut out of the gel and DNA extracted by MinElute Gel Extraction Kit, according to manufacturer's instructions (Qiagen, Valencia Calif.). Forward and reverse primers used in RT-PCR served as forward and reverse primers for sequencing using ABI Prism Big Dye Terminator v3.1 Cycle Sequencing Kit, according to manufacturer's instructions (Applied Biosystems, Foster City Calif.).

For immunohistochemistry, unstained slides were deparaffinized and stained with CONFIRM™ anti-ALK1 primary antibody (mouse monoclonal clone ALK01; Ventana Medical Systems, Tucson Ariz.). All immunohistochemistry steps were performed using the BenchMark XT, according to manufacturer's protocol (Ventana Medical Systems, Tucson Ariz.).

Results: A fluorescent RT-PCR assay was designed utilizing a single FAM-labeled ALK exon 20 reverse primer and 22 forward primers for each of the first 22 exons of EML4 (Table 2). The forward primers were split into 4 separate reactions, all containing the labeled ALK exon 20 reverse primer. Upon fragment analysis, each known EML4-ALK fusion variant would yield a specific size that is utilized to identify the fusion(s) present. Furthermore, potential exon fusions would yield a unique size product for ease of identification of EML4 exon involvement, assuming no insertions or deletions are present (Table 3).

TABLE 3

Expected amplicon size by variant

| EML4|ALK variant | EML4 exon involvement | Multiplex Reaction# | Amplicon Size (bp) |
|---|---|---|---|
| Published EML4-ALK fusion variants | | | |
| 2, 3a, 3b, 4, 7, E20; ins18A20 | 20, 6, 14, 20 | 1 | 183, 112, 145, 163, 187, 201 |
| "V5" | 18 | 2 | 167 |
| 1, 6, E17; ins68A20 | 13, 17 | 3 | 146, 215, 144 |
| "V4", 5a, 5b | 15,2 | 4 | 134, 118, 235 |
| Potential EML4 exon involvement* | | | |
| Unknown | 1, 5, 9, 12, 16, 21 | 2 | 152, 199, 137, 181, 186, 170 |

TABLE 3-continued

Expected amplicon size by variant

| EML4\|ALK variant | EML4 exon involvement | Multiplex Reaction# | Amplicon Size (bp) |
|---|---|---|---|
| Unknown | 3, 7, 10, | 3 | 154, 170, 187, |
| Unknown | 4, 8, 11, 19, 22 | 4 | 144, 183, 131, 168, 137 |

*Amplicon sizes are estimated based on no insertions or deletions

Screening of 55 NSCLC formalin-fixed paraffin embedded (FFPE) tumor tissue samples resulted in detection of 9.1% (5/55) EML4-ALK fusion positive cases, all of which were classified as adenocarcinoma (Table 4). Four of the positive cases harbored previously described fusion variants, the majority of which were variants 3a and/or 3b (3/5) and one variant 1 (Table 5).

TABLE 4

Distribution of EML4-ALK positive tumors by NSCLC subtype.

| Subtype | n | EML4-ALK Positive |
|---|---|---|
| Total | 55 | 9.1% (5/55) |
| Adenocarcinoma | 37 | 13.5% (5/37) |
| Squamous cell | 11 | 0% |
| Adenosquamous | 5 | 0% |
| Large cell carcinoma | 2 | 0% |

TABLE 5

Distribution of EML4-ALK fusion variants.

| EML4-ALK | Positive | Variant Reference |
|---|---|---|
| Total | 9.1% (5/55) | See below |
| Variant 1 | 1.8% (1/55) | Soda et al., 2007 |
| Variant 2 | 0% | Soda et al., 2007 |
| Variant 3a | 5.3% (3/55) | Choi et al., 2008 |
| Variant 3b | 3.5% (2/55) | Choi et al., 2008 |
| Variant 4 | 0% | Takeuchi et al., 2008 |
| Variant "4" | 0% | Koivunen et al., 2008 |
| Variant 5a | 0% | Takeuchi et al., 2008 |
| Variant 5b | 0% | Takeuchi et al., 2008 |
| Variant "5" | 0% | Wong et al., 2009 |
| Variant 6 | 0% | Takeuchi et al., 2009 |
| Variant 7 | 0% | Takeuchi et al., 2009 |
| Variant 8a | 1.8% (1/55) | Present study |
| Variant 8b | 1.8% (1/55) | Present study |
| Variant E17 | 0% | Tokahashi et al., 2009 |
| Variant E20 | 0% | Tokahashi et al., 2009 |

In addition, one case yielded 2 strong amplification peaks at unexpected sizes in the reaction containing EML4 exon 3, 7, 10, 13, and 17 (master mix #3). In order to identify the EML4 exon involvement, separation of the primers into individual reactions revealed that both peaks resulted from amplification with the EML4 exon 17 forward primer yielding 2 amplicons of 170 bp and 237 bp (FIG. 1A). ALK rearrangement was also confirmed by fluorescence in situ hybridization (FISH) using break apart probes to detect rearrangements at the 2p23 locus. Both haploid and diploid cells were observed in the specimen harboring novel variants 8a/b, where split signal from the 5' and 3' ALK probes were evident (data not shown).

Twenty-two additional specimens (3 more EML4-ALK positive and 19 negative by RT-PCR) were also confirmed by FISH as described above for a total of 23 of the 55 specimens (data not shown). Due to limited sample, FISH was not performed on the variant 1 positive specimen. All specimens that tested negative by RT-PCR also tested negative by FISH. Three of the four total RT-PCR positives tested were also positive by FISH. One sample tested positive for EML4-ALK fusion variants 3a and 3b by RT-PCR, but negative for by FISH. Upon repeat RNA extraction and RT-PCR, detection of variant 3a and 3b in this specimen by RT-PCR was duplicated. These results suggest higher sensitivity of the RT-PCR assay.

Sequencing of the un-identified amplicons described above demonstrated that both amplicons were composed of complete EML4 exon 17 and ALK exon 20, differing in size based on varying partial intron insertions. The 170 bp peak (variant 8a) consisted of EML4 exon 17 fused to ALK exon 20 containing a 30 nucleotide intron 19 insertion, E17; ins30A20 (FIG. 1B). The 237 bp peak (variant 8b) consisted of EML4 exon 17, with an insertion of 61 non-adjacent nucleotides from intron 17, fused to ALK exon 20 with a 34 nucleotide insertion from intron 19, E17ins61; ins34A20 (FIG. 1C). As a result, the two fusion products formed likely consist of EML4 exon 1-17 and ALK 20-29 with a 30 bp (8a) or 95 bp (8b) insertion (FIG. 2A).

In order to determine whether the EML4 intron 17 segment may be observed adjacent to exon 17 as a result of alternative splicing in normal EML4 transcripts, RT-PCR was performed on 3 NSCLC cell lines (NCI-H2228, NCI-1299, NCI-H838), two normal lung cancer tissues and the variant 8a/b positive lung cancer tissue using primers specific to exon 17 and the 61 bp intron 17 segment. The only specimen that resulted in an amplicon of expected size was the variant 8a/b positive lung cancer specimen (data not shown). This suggests that as a result of this specific paracentric inversion, a new alternative splice site is created in the pre-mRNA transcript.

Figure 2B:
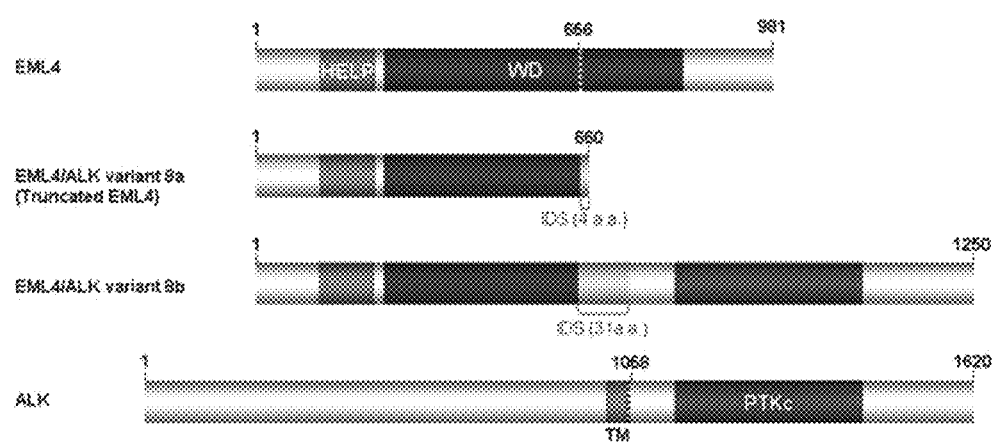

Based on the deduced amino acid sequence, the translated variant 8a protein yields a 660 a.a. protein (SEQ ID NO: 29) and variant 8b yields a 1250 a.a. protein (SEQ ID NO: 30), shown below. Fusion variant 8a appears to encode an EML4 truncation with no functional ALK domains resulting from the presence of an early stop codon located in the 30 bp insertion (FIG. 2B). However, variant 8b contains an in-frame 95 bp insertion resulting in the presence of a putatively functional ALK protein tyrosine kinase domain (underlined amino acids in SEQ ID NO: 30 below). (See FIG. 2B).

```
                                        (SEQ ID NO: 29)
MDGFAGSLDDSISAASTSDVQDRLSALESRVQQQEDEITVLKAALADVLRR

LAISEDHVASVKKSVSSKGQPSPRAVIPMSCITNGSGANRKPSHISAVSIA

GKETLSSAAKSGTEKKKEKPQGQREKKEESHSNDQSPQIRASPSPQPSSQP

LQIHRQTPESKNATPIKSIKRPSPAEKSHNSWENSDDSRNKLSKIPSTPKL

IPKVIKTADKHKDVIINQEGEYIKMFMRGRPITMFIPSDVDNYDDIRTELP

PEKLKLEWAYGYRGKDCRANVYLLPTGEIVYFIASVVVLFNYEERTQRHYL

GHTDCVKCLAIHPDKIRIATGQIAGVDKDGRPLQPHVRVWDSVILSTLQII

GLGTFERGVGCLDFSKADSGVHLCVIDDSNEHMLIVWDWQKKAKGAEIKTT

NEVVLAVEFHPIDANTIITCGKSHIFFWIWSGNSLTRKQGIFGKYEKPKFV

QCLAFLGNGDVLIGDSGGVMLIWSKTIVEPTPGKGPKGVYQISKQIKAHDG
```

-continued
SVFILCQMRNGMLLIGGGKDRKIILWDHDLNPEREIEVPDQYGTIRAVAEG

KADQFLVGISRNFILRGTENDGFQIEVQGHTDELWGLATHPFKDLLLICAQ

DRQVCLWNSMEHRLEWTRLVDEPGHCADFHPSGTVVAIGTHSGRPCCS (SEQ ID NO: 30)
MDGFAGSLDDSISAASTSDVQDRLSALESRVQQQEDEITVLKAALADVLRR

LAISEDHVASVKKSVSSKGQPSPRAVIPMSCITNGSGANRKPSHISAVSIA

GKETLSSAAKSGTEKKKEKPQGQREKKEESHSNDQSPQIRASPSPQPSSQP

LQIHRQTPESKNATPIKSIKRPSPAEKSHNSWENSDDSRNKLSKIPSTPKL

IPKVIKTADKHKDVIINQEGEYIKMFMRGRPITMFIPSDVDNYDDIRTELP

PEKLKLEWAYGYRGKDCRANVYLLPTGEIVYFIASVVVLFNYEERTQRHYL

GHTDCVKCLAIHPDKIRIATGQIAGVDKDGRPLQPHVRVWDSVILSTLQII

GLGTFERGVGCLDFSKADSGVHLCVIDDSNEHMLIVWDWQKKAKGAEIKTT

NEVVLAVEFHPIDANTIITCGKSHIFFWIWSGNSLTRKQGIFGKYEKPKFV

QCLAFLGNGDVLIGDSGGVMLIWSKTIVEPTPGKGPKGVYQISKQIKAHDG

SVFILCQMRNGMLLIGGGKDRKIILWDHDLNPEREIEVPDQYGTIRAVAEG

KADQFLVGISRNFILRGTENDGFQIEVQGHTDELWGLATHPFKDLLLICAQ

DRQVCLWNSMEHRLEWIRLVDEPGHCADFHPSGTVVAIGTHSGRRQKHEVN

FPKIKLIKKCGMLPGHVAADHPPAVYRRKHQELQAMQMELQSPEYKLSKLR

ISTIMIDYNPNYCFAGKISSISDLKEVPRKNITLIRGLGHGAFGEVYEGQV

SGMPNDPSPLQVAVKILPEVCSEQDELDFLMEALIISKFNHQNIVRCIGVS

LQSLPRFILLELMAGGDLKSFLRETRPRPSQPSSLAMLDLLHVARDIACGC

QYLEENHFIHRDIAARNCLLTCPGPGRVAKIGDFGMARDIYRASYYRKGGC

AMLPVKWMPPEAFMEGIFTSKIDTWSFGVLLWEIFSLGYMPYPSKSNQEVL

EFVTSGGRMDPPKNCPGPVYRIMTQCWQHQPEDRPNFAIILERIEYCTQDP

DVINTALPIEYGPLVEEEEKVPVRPKDPEGVPPLLVSQQAKREEERSPAAP

PPLPTISSGKAAKKPTAAEISVRVPRGPAVEGGHVNMAFSQSNPPSELHKV

HGSRNKPISLWNPTYGSWFTEKPIKKNNPIAKKEPHDRGNLGLEGSCIVPP

NVATGRLPGASLLLEPSSLTANMKEVPLFRLRHFPCGNVNYGYQQQGLPLE

AATAPGAGHYEDTILKSKNSMNQPGP

To determine whether a functional EML4-ALK fusion protein was present in the tumor tissue, immunohistochemistry (IHC) of the tissue with ALK1 monoclonal antibodies was performed. IHC confirmed significant ALK1 staining of the cytoplasm in tumor cells, indicating overexpression of the ALK domain of the fusion protein in the malignant cells (data not shown). Furthermore, nine additional specimens (1 more positive and 8 negative by RT-PCR) were confirmed by IHC for a total of 10 of the 55 specimens. In total, 2 RT-PCR positive cases were also positive by IHC and 8 RT-PCR negative cases were also negative by IHC.

Using this method to screen a relatively small cohort of NSCLC specimens (n=55) we were able to identify three previously described EML4-ALK fusion variants (1, 3a and 3b) as well as an additional two novel variants involving exon 17 of EML4 (8a and 8b) in 9.1% (5/55) of the NSCLC specimens examined. Notably, EML4 exon 17 to ALK exon 20 fusions will not yield an in-frame fusion unless they possess insertions or deletions to create an in-frame fusion. In fact, one fusion variant that we observed (8a) contained an insertion of 30 bp that results in an early stop codon and would not likely have malignant transforming activity on its own. This particular case also expressed variant 8b, with a 95 bp insertion, which is most likely responsible for expression of the ALK domain in this specimen as observed by IHC and the transformation or malignant phenotype.

An interesting feature of variant 8b was the presence of a 61 bp sequence of non-adjacent EML4 intron 17. This intron sequence is located ~1.2 kb down stream of exon 17 in the normal EML4 transcript. Based on analysis of normal lung tissue and non-variant 8b containing cells, it is clear that this configuration of intron 17 is not a result of normal alternative splicing but rather alternative splicing that appears as a result of translocation.

Unless otherwise defined, all technical and scientific terms used herein have the same meaning as commonly understood by one of ordinary skill in the art to which this invention belongs. All nucleotide sequences provided herein are presented in the 5' to 3' direction.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

What is claimed is:

1. A method for detecting the presence or absence of EML4-ALK gene fusion variants in a nucleic acid sample from a subject, comprising amplifying nucleic acids in the sample using a set of forward primers in a multiplex reaction, wherein each primer binds to one of EML4 exons 1-22, and a reverse primer that binds to ALK exon 20; and detecting the EML4-ALK gene fusion variants in the amplified nucleic acids, wherein the set of forward primers comprises a forward primer comprising SEQ ID NO: 19.

2. The method of claim 1, wherein detecting the EML4-ALK gene fusion variants comprises capillary electrophoresis of the amplified nucleic acids.

3. The method of claim 1, wherein detecting the EML4-ALK gene fusion variants comprises sequencing the amplified nucleic acids.

4. The method of claim 1, wherein a nucleic acid comprising SEQ ID NO: 1 or SEQ ID NO: 2 is amplified.

5. The method of claim 1, wherein the set of forward primers are selected from the group consisting of SEQ ID NOs: 3-24.

6. The method of claim 1, wherein the reverse primer comprises SEQ ID NO: 25.

7. The method of claim 1, wherein the sample is from a subject suspect of having a neoplastic disorder.

8. The method of claim 7, wherein the neoplastic disorder is non-small cell lung cancer.

9. The method of claim 1, wherein the sample is selected from the group consisting of plasma, serum, and biopsy tissue.

10. The method of claim 9, wherein the sample is a lung biopsy sample.

* * * * *